United States Patent [19]
Härle

[11] Patent Number: 5,693,099
[45] Date of Patent: Dec. 2, 1997

[54] ENDOPROSTHESIS

[76] Inventor: Anton Härle, Drechslerweg 40, D-4400 Münster-Roxel, Germany

[21] Appl. No.: 1,496

[22] Filed: Jan. 7, 1993

[51] Int. Cl.⁶ .................. A61F 2/28; A61F 1/04; A61F 2/32
[52] U.S. Cl. .................. 623/16; 606/94; 623/23
[58] Field of Search .................. 623/16, 18, 19, 623/20, 23; 606/93, 94

[56] References Cited

U.S. PATENT DOCUMENTS

| 4,274,163 | 6/1981  | Malcom et al. | 623/20 |
| 5,274,163 | 12/1993 | Malcom        | 623/20 |
| 5,340,362 | 8/1994  | Carbone       | 623/2.23 |

FOREIGN PATENT DOCUMENTS

| 0331623 | 9/1989  | European Pat. Off. | 623/23 |
| 0434604 | 6/1991  | European Pat. Off. | 623/23 |
| 0462357 | 12/1991 | European Pat. Off. | 623/23 |
| 0487433 | 5/1992  | European Pat. Off. | 623/23 |
| 3331091 | 3/1985  | Germany .          |        |
| 3704089 | 8/1988  | Germany            | 623/23 |
| 3704089 | 10/1990 | Germany .          |        |
| 3912465 | 11/1990 | Germany .          |        |
| 9108720 | 6/1991  | WIPO               | 623/23 |

*Primary Examiner*—David Isabella
*Attorney, Agent, or Firm*—Peter K. Kontler

[57] ABSTRACT

A prosthesis which can be implanted into the cavity of a bone or between spaced apart bones defines a passage with ports for evacuation of air and/or other matter from the cavity or cavities which are to receive bone cement or other cement. The prosthesis is inserted and centered prior to introduction of cement, and its passage or passages are connected to a suction generating device during admission of cement. If necessary, the prosthesis can be confined in a jacket to prevent overheating of adjacent tissue during polymerization of the introduced mass of cement. The passage or passages in the prosthesis can be filled with cement and/or with medications which penetrate into the adjacent tissue subsequent to implantation of the prosthesis.

8 Claims, 2 Drawing Sheets

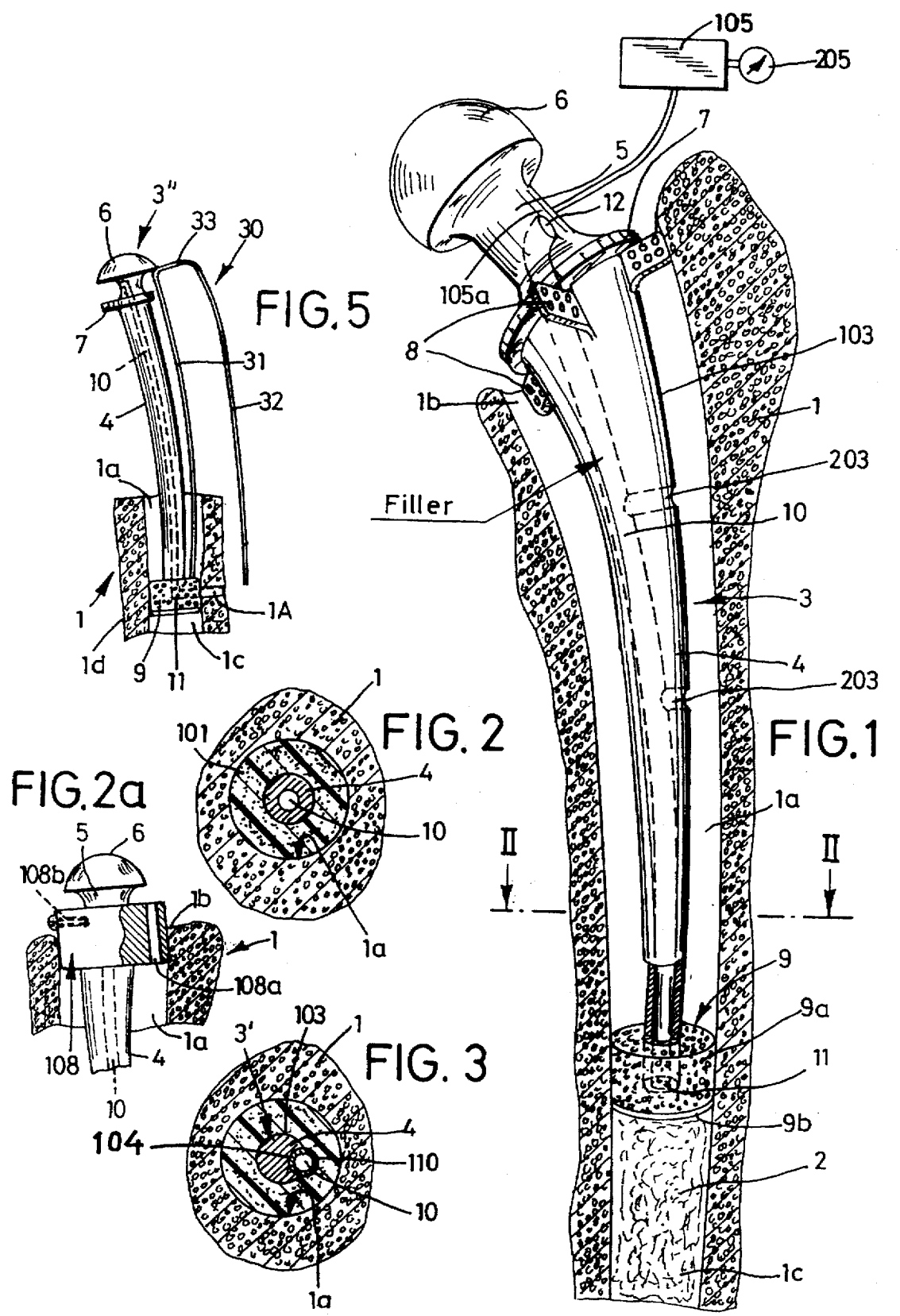

ENDOPROSTHESIS

BACKGROUND OF THE INVENTION

The invention relates to endoprostheses in general, and more particularly to improvements in prostheses which are to be implanted into bone cavities or into cavities between bones as substitutes for portions of bones or entire bones.

An endoprosthesis will be implanted into an animal body to constitute or to form part of an artificial joint (such as a knee joint, a hip joint, an elbow joint or a shoulder joint), or to replace one or more bones (e.g., one or more vertebrae and/or one or more discs in a spinal column). Proper implantation of an endoprosthesis necessitates satisfactory stabilization of the prosthesis in the surrounding tissue, e.g., in the cavity of a femur or another bone. In many instances, the implantation of an endoprosthesis brings about the danger of infection which, in turn, entails a loosening of the implanted prosthesis. In fact, an infection resulting from the implantation of a prosthesis, or complications attributable to an infection, can constitute a threat to the life of the patient.

Heretofore known procedures involving implantation of a prosthesis in an animal body, and more particularly in the cavity of a bone, include the so-called press-fit anchoring which involves the establishment of congruence between the bearing (i.e., the bone) and the implanted prosthesis. In other words, the prosthesis completely fills a properly shaped cavity in a bone, e.g., in the femur of a human patient. Such mode of implantation is complex because it necessitates highly accurate treatment of the surface surrounding the bone cavity and extremely high accuracy during implantation of the prosthesis into such cavity. Moreover, the implanted prosthesis is likely to become loose because the modulus of elasticity of the bone is different from the modulus of elasticity of the (normally metallic) material of the implanted prosthesis. This problem which arises as a result of press-fit anchoring of an endoprosthesis is yet to be solved in a satisfactory manner.

In view of the above outlined problems which arise by resorting to press-fit anchoring of an endoprosthesis in the cavity of a bone, it is often preferred to employ a suitable bone cement which is introduced into a bone cavity or between bones to surround the implanted portion of the prosthesis and to establish a reliable bond between the bone and the implant. The layer of introduced cement between the implant and the tissue surrounding the cavity acts not unlike a buffer and protects the bone from excessive stresses.

However, presently known implantations with bone cement also present numerous problems. For example, heretofore known techniques cannot invariably ensure complete filling of a bone cavity with bone cement so that the theoretically achievable beneficial effects of a predictable buffer between the implant and the surrounding portion of a bone are not always achieved or are not achievable at all. One of the most serious problems to be solved in connection with the cementing of a portion of a prosthesis in the cavity of a bone is that of ensuring homogenous filling of the cavity with suitable bone cement. For example, if the cement is introduced in batches, it is practically unavoidable that certain quantities of air and/or blood will penetrate into the cavity and will be entrapped in the introduced cement, particularly between successively introduced batches of cement. This entails lamination of the cement and a pronounced reduction of mechanical strength of the hardened mass which fills the cavity around the implanted portion of a prosthesis.

If the cement is introduced into a bone cavity prior to insertion of a portion of an endoprosthesis, the introduced portion of the prosthesis is likely to come close to or to actually rub against certain portions of bone tissue around the cavity which contains the cement. This holds particularly true if the cavity in the bone has an arcuate shape. It happens again and again that certain portions of the implant are in direct contact with bone tissue, i.e., that there is no buffer of cementitious material between such parts. This necessarily results in the development of peak stresses at the point or points of direct contact between the implant and bone tissue, and such stresses can be sufficiently pronounced to cause cracking or complete breaking of hardened cement and/or even damage to (such as breaking of) the implanted prosthesis.

Another drawback of presently known procedures which involve the introduction of a portion of an endoprosthesis into a bone cavity is that the prosthesis causes a pronounced rise of pressure upon the marrow in the bone cavity. The pressure can rise to a value which entails expulsion of fat from bone marrow. This can result in embolism. Therefore, it was already proposed to evacuate air from the cavity which is to receive bone cement and to introduce such cement by suction. One presently known proposal involves the making of a hole in the bone adjacent the innermost part of that portion of the bone cavity which is to be filled with cement. The opening is connected to the intake of a suction generating device and nonpolymerized cement is drawn through the open end of and into the cavity, i.e., from that end of the cavity which is open in order to permit introduction of a selected portion of a prosthesis. Such introduction normally takes place prior to insertion of a portion of the prosthesis into the cavity.

The just outlined proposal is not entirely satisfactory because the introduction of a portion of an endoprosthesis into the prepared cavity of a bone still results in a pronounced rise of pressure upon the marrow in the adjacent non-evacuated portion of the bone cavity. Moreover, a certain undercutting of previously introduced bone cement cannot be avoided during subsequent insertion of a selected portion of an endoprosthesis so that the mass of bone cement in the cavity invariably, or at least frequently, surrounds empty spaces. This is particularly difficult to avoid if the cavity is not straight so that the introduced portion of the prosthesis is likely to rub against bone tissue at the bend or bends with the resulting stripping of cement from such location or locations.

Another drawback of the just discussed conventional methods of relying on suction for introduction of bone cement is that the opening or openings which are provided for evacuation of air from the cavity of a bone prior to and during introduction of bone cement unduly weaken the bone. Thus, the bone is likely to break at the opening or openings. Moreover, the opening or openings must be drilled at a location which is normally remote from the open end of the cavity. Therefore, it is necessary to make a relatively long incision for the sole purpose of reaching a proper location for the drilling of one or more openings into a bone at a location which is remote from the open end of the cavity for reception of an implant, or it is necessary to carry out a separate operation for the sole purpose of exposing that portion of the bone which is to be provided with one or more holes for evacuation of air preparatory to and during introduction of bone cement.

OBJECTS OF THE INVENTION

An object of the invention is to provide a novel and improved prosthesis which can be cemented into the cavity of a bone or into a cavity or gap between the bones in an animal body.

Another object of the invention is to provide a prosthesis which can be cemented in place in such a way that its retention in an optimum position is more reliable and longer lasting than that of heretofore known prostheses.

A further object of the invention is to provide a prosthesis which can be implanted into the cavity of a bone or otherwise in a simple, time-saving and efficient manner.

An additional object of the invention is to provide a prosthesis which can be uniformly surrounded with bone cement and whose implantation does not involve excessive pressurizing of marrow in the bone into which the prosthesis is to be implanted.

Still another object of the invention is to provide novel and improved means for preventing overheating of tissue during the setting of bone cement.

A further object of the invention is to provide a novel and improved indicating instrument or implement which can be utilized to facilitate proper implantation of a prosthesis in the cavity of a bone.

Another object of the invention is to provide a novel and improved method of introducing bone cement into an animal body during implantation of an endoprosthesis.

An additional object of the invention is to provide a novel and improved method of implanting a prosthesis in the spinal column of a patient.

Still another object of the invention is to provide a novel and improved method of introducing optimal quantities of cement into a bone or between bones as a step of implanting an endoprosthesis.

A further object of the invention is to provide a novel and improved arrangement for centering a portion of a prosthesis in the cavity of a bone.

Another object of the invention is to provide a prosthesis which is less likely to come in actual contact with bone tissue than heretofore known prostheses.

An additional object of the invention is to provide a novel and improved method of confining in an animal body one or more medications for penetration into or into contact with tissue upon completion of the implanting step.

Still another object of the invention is to provide a joint which embodies the above outlined prosthesis.

SUMMARY OF THE INVENTION

One feature of the present invention resides in the provision of a prosthesis for implantation into a bone, e.g., into a femur or into a spinal column. The improved prosthesis comprises a body having an external surface and provided with at least one suction passage and ports disposed at the external surface and communicating with the at least one passage. If the body of the prosthesis is elongated, the at least one suction passage can extend substantially longitudinally of such elongated body.

The at least one passage can be provided in an elongated central portion of the body of the prosthesis. Alternatively, the at least one passage can be provided adjacent the external surface of the body. For example, the body of the improved prosthesis can include a main portion and a second portion (e.g., in the form of an elongated tube, conduit or pipe) which is separably secured to the main portion; the at least one passage can be provided in the main portion or in the second portion. It is also possible to provide a passage in each portion of such composite body.

At least one end of the body of the improved prosthesis can be provided with a centering element. The centering element can be provided at the distal end of the body, namely at that end which is first to be inserted into the cavity of a bone and is remotest from the open end of such cavity when the inserting step is completed. The centering element can include a substantially impermeable portion which is disposed at a first distance from the proximal end of the body of the improved prosthesis and a permeable portion which is disposed at a lesser second distance from the proximal end. At least the permeable portion of the centering element can have the consistency of frit. The just discussed prosthesis can be used for implantation into a bone (e.g., a femur) having a cavity including an open end for introduction of at least a portion of the body of the prosthesis, and a portion which contains bone marrow and is spaced apart from the open end. The distal end of the body is receivable in the cavity adjacent the marrow-containing portion, and the centering element can constitute or resemble a plug which surrounds the distal end of the body and includes an impermeable portion adjacent the marrow and a permeable portion which is separated from the marrow by the permeable portion when the distal end of the body of the prosthesis is properly introduced into the cavity. One port of the body of such prosthesis can communicate with that unfilled portion of the cavity which is adjacent the open end by way of pores or channels in the permeable portion of the centering element.

The means for centering the inserted portion of the body of the aforediscussed prosthesis at the open end of the cavity in a bone can comprise one or more projections (e.g., in the form of permanently connected or separable fingers, prongs or analogous parts) which extend from the external surface of the body. Alternatively, or in addition to prongs or like parts, the centering means at the proximal end of the body of the improved prosthesis can comprise a collar which surrounds the body and enters the open end of the cavity in a bone prior to introduction of bone cement into the cavity by way of the open end, preferably through one or more holes in the collar.

The centering device or element at the distal end and/or the centering means at the proximal end can be separably connected to the body of the improved prosthesis. The means for separably connecting the centering element and/or the centering means to the body can include screws, bolts, pins or other suitable fasteners.

The body of the prosthesis can be provided with at least one outlet to dispense a medicine into the tissue surrounding the external surface of the implanted portion of the body. The at least one outlet can be constituted by one of the aforementioned ports or such outlet can be provided in addition to the ports.

The body of the prosthesis can comprise at least two parts (e.g., acting not unlike the leaves of a hinge or the mutually movable parts of a universal joint) and means (e.g., a substantially spherical head or a pintle) for articulately connecting the parts to one another.

The prosthesis can further comprise a foraminous reinforcing filler in the at least one passage. Such filler can be made of sintered metallic or vitreous material and can constitute a permeable stabilizing core or insert in the at least one passage of the body of the prosthesis.

The prosthesis can be furnished with one or more supplies of a medicine which is introduced into the at least one passage upon completion of implantation of the body in a bone so that the medicine can issue from the passage and exert a beneficial effect upon the adjacent tissue.

Another feature of the invention resides in the provision of a kit including a prosthesis for implantation into an open-ended cavity of a bone and an indicating implement. The prosthesis comprises a body having an external surface, a proximal end and a distal end and may include at least one elongated passage extending between the proximal and distal ends of the body. If the body has one or more passages, it is preferably further provided with at least one port at the distal end and with at least one port at the proximal end, and each of these ports communicates with the at least one passage. Still further, the prosthesis can include a centering element at the distal end of the body, and such distal end is insertable through the open end and into the cavity of a bone to locate the centering element at a selected distance from the open end. The indicating implement serves to pinpoint the location of the centering element and/or of the port or ports at the distal end at the outer side of the bone upon insertion of the distal end into the cavity so that a surgeon can drill a hole from the outer side of the bone toward and into communication with the cavity at the centering element. This hole can be used to permit evacuation of air from the cavity preparatory to admission of flowable bone cement through the open end of the cavity. Such evacuation can take place in addition to or in lieu of evacuation of air from the cavity through the port or ports at the distal end of the body, through the passage or passages and through the port or ports at the proximal end of the body.

The indicating implement can comprise or constitute a substantially U-shaped tool including a first leg having an end at the centering element and/or at the port or ports in the distal end of the body of the prosthesis, and a second leg having an end in a predetermined position relative to the end of the first leg. The first leg is insertable into the cavity with the body of the prosthesis, and the second leg is then located adjacent the outer side of the bone upon insertion of the body into the cavity so that the end of the second leg pinpoints the location of the centering element and/or of the port or ports at the distal end.

A further feature of the invention resides in the provision of a prosthesis serving for implantation into a bone (e.g., into a spinal column) and comprising a body having an external surface and provided with at least one suction passage and ports disposed at the external surface and communicating with the at least one passage. The prosthesis is used in conjunction with a jacket which surrounds at least a portion of the body of the prosthesis and has at least one opening in communication with one of the ports in the body of the prosthesis. The prosthesis and the jacket can be furnished with means for evacuating air from the at least one passage through the one port and the at least one opening prior to or simultaneously with admission of flowable cement into the thus evacuated passage.

The jacket can be made, at least in part, of a suitable heat insulating material. Alternatively, or in addition to such selection of the material of the jacket, the latter can be provided with cooling means. The jacket can be constructed and assembled to separably surround the body of the prosthesis during introduction of cement and during setting of introduced cement. To this end, the jacket can be assembled of a plurality of separable sections, e.g., of two semicylindrical shells which can be placed around a cylindrical body forming part of the prosthesis.

The prosthesis can further comprise means for connecting or securing the body to the bone. Such securing or connecting means can comprise at least one projection (e.g., an elongated strip-shaped member or a substantially L-shaped bracket) provided on and extending from the external surface of the body, and at least one fastener for affixing the at least one projection to the bone. Alternatively, or in addition to the just described connecting means, the means for securing the body of the prosthesis to a bone (for example, to two neighboring vertebrae of a spinal column), can comprise at least one socket provided in the body of the prosthesis and one or more fasteners serving to cooperate with the socket or sockets to affix the body of the prosthesis to a bone.

The novel features which are considered as characteristic of the invention are set forth in particular in the appended claims. The improved endoprosthesis itself, however, both as to its construction and the mode of implanting the same, together with additional features and advantages thereof, will be best understood upon perusal of the following detailed description of certain presently preferred specific embodiments with reference to the accompanying drawings.

BRIEF DESCRIPTION OF THE DRAWINGS

FIG. 1 is a fragmentary sectional view of a femur and of a prosthesis which embodies one form of the invention and is centered in the cavity of the femur preparatory to introduction of bone cement;

FIG. 2 is a sectional view substantially as seen in the direction of arrows from the line II—II in FIG. 1 and shows a mass of hardened cement in the bone cavity around the implant;

FIG. 2a is a fragmentary longitudinal sectional view of a modified prosthesis having different centering means;

FIG. 3 is a sectional view similar to that of FIG. 2 but showing a further prosthesis;

FIG. 5 is a fragmentary schematic sectional view somewhat similar to that of FIG. 1 and further showing an implement serving to pinpoint the locus of a centering device upon insertion of a portion of a prosthesis into the cavity of a bone.

DESCRIPTION OF PREFERRED EMBODIMENTS

Figure 4:
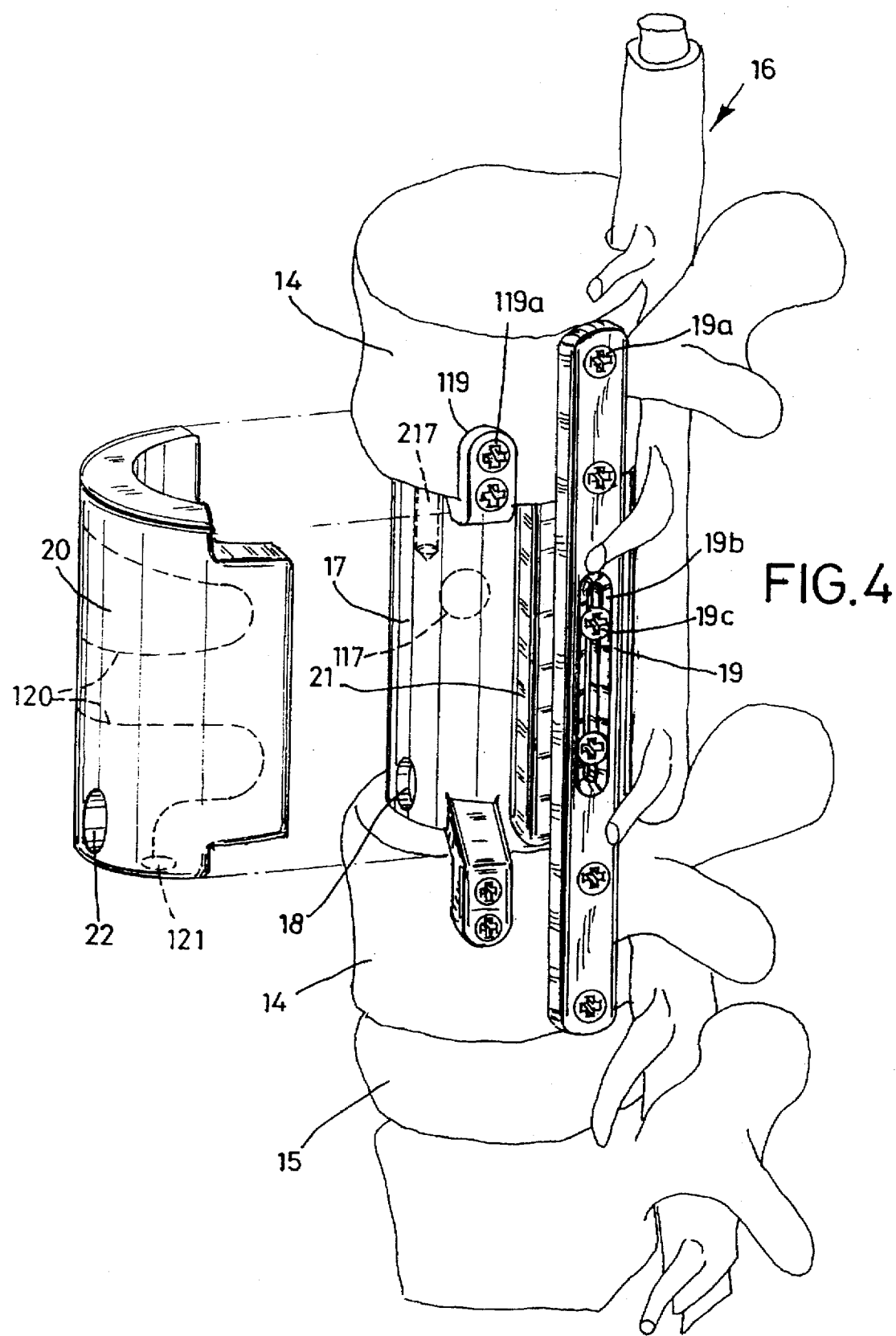
FIG. 4 is a partly exploded perspective view of a portion of a spinal column with spinal cord, of a prosthesis between two vertebrae of the spinal column, and of a jacket which surrounds the prosthesis to shield the spinal cord from overheating during setting of cement.

FIG. 1 shows a portion of a femur 1 having a cavity 1a with an open end at 1b and a portion 1c filled with bone marrow 2. The part of cavity 1a between the portion 1c and the open end 1b was treated with a suitable milling or grating tool (not shown because not forming part of the invention) to provide room for insertion of the major part of the body of an elongated endoprosthesis 3 and of bone cement 101 (FIG. 2) around the external surface 103 of the body. The evacuated portion of the cavity 1a between the portion 1c and the open end 1b has a predetermined shape to receive the major part of the body of the prosthesis with a certain amount of clearance so as to provide adequate space for introduction of cement 101.

The body of the prosthesis 3 comprises an elongated stem or shank 4, a neck 5 at one end of the shank 4, a head 6 which is receivable in the socket of the hip joint in a patient's body, and a flange 7 between the shank 4 and the neck 6. When the prosthesis 3 is properly implanted in the cavity 1a (see FIG. 2), the distal end (namely the free end of the shank 4) of the body 4–7 is located in the cavity 1a at a predetermined distance from the open end 1b, and the proximal end of the body 4–7 (such proximal end includes the head 6, the neck 5 and the flange 7) is located outside of and at the open end 1b of the cavity 1a.

The prosthesis 3 further comprises a centering device 9 in the form of a plug which surrounds the distal end of the body, and centering means including several projections 8 provided on the shank 4 adjacent the flange 7 and being distributed, oriented and dimensioned to extend from the external surface 103 of the body and to abut the surface surrounding the open end 1b when the prosthesis 3 is properly inserted into the cavity 1a between the open end 1b and the portion 1c. The illustrated centering projections 8 are discrete fingers or prongs which are of one piece with the shank 4 and/or with the flange 7 and are or can be provided with holes or bores for reception of some of the bone cement 101 when such substance fills the space between the external surface of the shank 4 and the surface surrounding the corresponding portion of the cavity 1a between the open end 1b and the marrow-containing portion 1c.

The centering means including the projections or fingers 8 can be replaced with centering means of the type shown in FIG. 2a, namely a centering means consisting of or comprising a collar 108 provided with one or more apertures 108a (e.g., in the form of bores or holes) for admission of flowable bone cement into the cavity 1a. One or more screws 108b or other suitable fasteners can be provided to separably secure the collar 108 to the shank 4. The collar 108 can replace the flange 7 and can be detached from the shank 4 and removed from the open end 1b when its centering section is no longer necessary because the cement has set around the implanted shank 4.

The centering means 8 can also constitute a separately produced component of the prosthesis 3 which is separably affixed to the flange 7 and/or to the shank 4 and is put to use to adequately center the proximal end of the prosthesis preparatory to and during introduction of bone cement 101. The separately produced centering means is thereupon removed from the body of the implanted prosthesis so that the proximal end of the body of such prosthesis is centered only by the hardened bone cement 101.

It is also possible to omit the discrete centering projections in the form of fingers or prongs 8 of FIG. 1 and to design the flange 7 in such a way that it includes a collar corresponding to the collar 108 of FIG. 2a and serving as a means for centering the proximal end of the body of the prosthesis 3 at the open end 1b of the cavity 1a. All that counts is to provide suitable means for at least temporarily centering the proximal end of the prosthesis 3 preparatory to and during introduction of cement 101 so that each and every portion of the shank 4 in the cavity 1a is surrounded by a requisite quantity of hardened cement when the introduced viscous material sets to anchor the shank 4 in bone 1.

The centering device or plug 9 at the portion 1c of the cavity 1a is preferably permeable, at least in part, and can have the consistency of frit. Alternatively, the plug 9 can be provided with pronounced channels for the passage of air in order to reduce the pressure in the cavity 1a between the portion 1c and the open end 1b preparatory to and during introduction of flowable cement 101.

In accordance with a feature of the invention, the body of the prosthesis 3 is provided with at least one suction or vacuum passage 10. FIG. 1 shows a single elongated passage 10 which is provided in the central portions of the shank 4 and flange 7 and communicates with two lateral ports 11 and 12. The port 11 is located at the external surface 103 of the body of the prosthesis 3 and is surrounded by the centering plug 9 so that it can communicate with the cavity 1a between the portion 1c and the open end 1b through the pores or channels of the plug 9. The port 12 is also provided at the external surface 103 of the body 4–7 of the prosthesis 3 and is machined into or is otherwise formed in the neck 5, i.e., the port 12 is accessible upon insertion of the shank 4 and plug 9 into the cavity 1a. If the intake 105a of a suction generating device 105 is introduced into or placed adjacent the port 12 and the suction generating device 105 is in operation, the pores or channels of the plug 9, the port 11, the passage 10 and the port 12 establish a path for evacuation of air from the cavity 1a between the open end 1b and the portion 1c (plug 9) so that a mass of still viscous cement 101 can be admitted into the cavity 1a through the open end 1b (around the flange 7 and between the centering projections 8) to completely fill the cavity between the plug 9 and the open end 1b.

The centering projections 8 cooperate with the centering plug 9 to ensure that the shank 4 of the body of the prosthesis 3 is properly centered in the cavity 1a between the open end 1b and the portion 1c prior to admission of cement 101 around the flange 7 and between the projections 8. The arrangement is preferably such that the external surface of the shank 4 is disposed substantially centrally of that portion of the cavity 1a which extends from the open end 1b to the portion 1c. Such positioning of the shank 4 in the cavity 1 ensures that the entire shank is surrounded by a mass of hardened bone cement whose thickness is at least substantially constant all the way around the external surface 103. Introduction of bone cement 101 around the flange 7 and between the projections 8 takes place while the shank 4 is being centered by the plug 9 and by the projections 8 and while the suction generating device 105 draws air from the cavity 1a via pores or channels of the plug 9, port 11, passage 10 and port 12. Once the cavity 1a is filled with bone cement 101 and the introduced mass of bone cement hardens, the shank 4 is permanently implanted in the femur 1 and the hardened cement fills the cavity 1a from the plug 9 to the open end 1b.

Introduction of still flowable bone cement 101 takes place around the flange 7 and between the tips of the projections 8 while the suction generating device 105 draws air from the cavity 1a through the permeable portion of the plug 9, port 11, passage 10 and port 12. This ensures that the cavity 1a is completely filled with cement 101 while the suction generating device 105 is on to draw air from the cavity 1a through the port 11, passage 10 and port 12. It is clear that the number of ports 11 and/or 12 can be increased to two or more without departing from the spirit of the invention.

The admission of flowable bone cement 101 into the open end 1b of the cavity 101a can be interrupted in response to detection that the resistance to further evacuation of air from the cavity 1a via port 11, passage 10 and port 12 has risen to a predetermined value. This is the case when the centering plug 9 is provided with relatively small pores which permit air to flow from the cavity 1a into the passage 10 but oppose the flow of cement 101 into the port 11 and thence into the passage 10. Thus, a simple pressure gauge 205 on or at the suction generating device 105 suffices to indicate that the resistance to further evacuation of air from the cavity 1a has risen to a value which indicates that the cavity 1a is filled with cement 101 all the way between the flange 7 and the plug 9. The introduced mass of bone cement 101 in the cavity 1a between the open end 1b and the plug 9 is then caused or permitted to set and to thus reliably anchor the shank 4 in the femur 1.

The passage 10 can remain empty or it can be filled with a material which exhibits desirable mechanical and/or medicinal properties.

If the pores of the centering plug 9 are sufficiently large to permit penetration of cement 101 into the port 11 and thence into the passage 10, or if the upper portion (as viewed in FIG. 1) of the plug 9 is intentionally provided with one or more channels leading from the unoccupied portion of the cavity 1a into the port 11, admission of bone cement 101 into the open end 1b around the flange 7 is or can be interrupted when the cement fills the port 11 and the passage 10. The admission of flowable cement 101 can be selected in such a way that it is interrupted when the passage 10 is filled and the cement begins to issue at the port 12; this is possible if the pores and/or channels in the plug 9 are sufficiently large to permit flowable cement 101 to penetrate into the port 11 and thence into the passage 10 and, if desired, all the way into and from the port 12. In the latter instance, emergence of cement 101 at the port 12 is a highly reliable indicator that the cavity 1a is completely filled with cement 101 all the way from the open end 1b to the plug 9. The cement 101 can contain one or more pharmaceutical substances and/or other medicines which reduce the likelihood of infection in the passage 10 and/or at the ports 11 and 12 and/or elsewhere in the bone 1.

The permeability of a portion of or the entire centering plug 9 will be selected in dependency upon whether or not the passage 10 is to be filled with cement 101.

In order to ensure proper and long-lasting seating of the shank 4 of the body of the prosthesis 3 in the cavity 1a, it is desirable to make the prosthesis of a material having a modulus of elasticity which at least approximates the modulus of elasticity of the bone 1 around the cavity 1a. The modulus of elasticity of the material of the prosthesis 3 will be selected in dependency upon the characteristics of the material which constitutes the cement 101 and/or in dependency on the porosity or permeability of the plug 9, i.e., whether or not the cement is to penetrate into and to fill the passage 10. All of these variables can be taken into consideration in order to ensure that the shank 4 is properly embedded in bone cement 101 which fills the cavity 1a between the open end 1b and the portion 1c when the implantation of the shank 4 is completed and the introduced bone cement is permitted to set.

Proper centering of the shank 4 in the cavity 1a is desirable and advantageous on the additional ground that a mass of hardened bone cement 101 having a given preferably uniform or substantially uniform thickness exceeding a predetermined minimum thickness is less likely to crack or break in certain regions of the cavity 1a. Cracking and/or breaking of hardened bone cement 101 in the cavity 1a is detrimental to the stability and strength of the hardened mass of bone cement and is also likely to permit or cause, with time, damage to the adjacent portions of the bone 1. In other words, such dimensioning of the shank 4 and of the cavity 1a that the introduced hardened mass of cement 101 exhibits a predetermined minimum thickness and accurately centers the shank 4 in the cavity brings about a number of important advantages including the following: The uniform width of that portion of the cavity 1a which is filled with hardened cement 101 ensures an optimal mechanical transfer of forces from the prosthesis 3 to the surrounding portion of the bone 1. Secondly, one eliminates the resorbent attack through the cancellous tissue of the bone such as normally arises in the region of cracks or breaks in bone cement.

The centering plug 9 can be introduced into the cavity 1a simultaneously with the shank 4. Alternatively, the plug 9 is introduced in a first step and the shank 4 is inserted in a subsequent step. In the latter instance, the central or substantially central hole of the inserted plug 9 must receive the tip of the shank 4 (i.e., the distal end of the prosthesis 3) in such a way that the unoccupied portion of the cavity 1a around the inserted shank 4 will provide room for a mass of cement 101 having a desirable uniform thickness or minimum thickness to thus ensure satisfactory implantation of the prosthesis 3 in the bone 1. In either event, the dimensions of the hole in the plug 9 and the dimensions of the tip of the shank 4 are selected with a view to ensure an optimal positioning of the shank 4 in the cavity 1a prior to admission of flowable cement 101.

When the suction generating device 105 is started to draw air from the cavity 1a through the pores or channels of the centering plug 9, port 11, passage 10 and port 12, the pores or channels of the plug 9 permit air to flow from the cavity 1a into the port 11 whereby a mass of flowable cement 101 enters the cavity in the region around the periphery of the flange 7 to fill the cavity 1a in a direction toward and all the way to the plug 9. In order to prevent the suction generating device 105 from drawing marrow 2 from the portion 1c of the cavity 1a, the plug 9 can include a permeable portion or section 9a nearer to the proximal end of the prosthesis 3 and an impermeable or less permeable portion 9b which is adjacent the portion 1c of the cavity 1a and prevents penetration of marrow 2 into the port 11.

The provision of a centering plug 9 having two portions or sections 9a, 9b exhibiting different permeabilities is necessary only if the permeability of the portion through which air flows from the cavity 1a around the properly inserted shank 4 into the port 11 is such that the suction generating device 105 would be likely to draw marrow 2 from the portion 1c of the cavity 1a into the port 11 and thence into the passage 10. Thus, the permeability of the plug 9 will depend upon the viscosity of the cement 101 at the time such substance is being drawn into the cavity 1a around the flange 7 and/or upon the viscosity of bone marrow 2 and/or upon the partial vacuum in the cavity 1a (as established by the suction generating device 105) and/or the permeability of the plug 9. The provision of a centering plug having portions or sections exhibiting different permeabilities can be said to constitute a safety feature which ensures that flowable cement 101 can be readily drawn into the cavity 1a through the open end 1b (i.e., around the flange 7) while the bone marrow 2 is prevented from penetrating through the plug 9 and into the port 11.

FIG. 2 shows that the thickness of the mass of hardened cement 101 in the cavity 1a of the bone 1 is at least substantially constant all the way around the external surface of the implanted shank 4.

FIG. 3 shows that the passage 10 need not be provided in the central portion or section of the shank 4 but, instead, is provided adjacent to the external surface 103. To this end, the body of the prosthesis 3' comprises a first portion or section including the shank 4, the neck 5, the head 6 and the flange 7 (the parts 5, 6 and 7 are not shown in FIG. 3) and a tubular second portion or section 110 which defines the suction passage 10 and is adjacent the external surface of the shank 4. The tubular section 110 which is shown in FIG. 3 is partially recessed (as at 104) into the shank 4. However, it is equally possible to omit the recess 104 and to place the section 110 next to a shank of the type shown in FIG. 1 or 2, i.e., a shank having a substantially circular cross-sectional outline all the way from the distal end of the prosthesis 3' to the flange 7. The section 110 which is shown in FIG. 3 constitutes a separately produced tubular body of a suitable metallic material which may but need not be the same as the material of the other portion or section of the prosthesis 3'. The portion or section 110 is permanently or separably affixed to the shank 4.

The admission of cement 101 into the cavity 1a around the shank 4 which is shown in FIG. 3 can be terminated when the cavity is filled with cement or when the cavity 1a and the passage 10 in the section 110 are filled with such material.

An important advantage of the improved prosthesis is that it can be properly installed and centered in the cavity 1a prior to introduction of cement 101. This reduces and actually eliminates the likelihood of excessive compression of marrow 2 in the portion 1c of the cavity 1a and ensures more uniform and more predictable introduction of requisite quantities of cement. Moreover, even if the portion of the body of a prosthesis to be implanted in the bone 1 happens to touch or rub against the bone tissue during insertion into the cavity 1a but is spaced apart from the surrounding tissue when the inserting step is completed, the cavity 1a can be readily and reliably filled with cement 101 in such a way that the entire implanted portion of the body of the prosthesis is surrounded by a layer of cement. Introduction of a homogeneous mass of cement 101 into the cavity 1a upon completed insertion of the shank 4 results in the formation of a layer of hardened cement which exhibits highly satisfactory mechanical strength and other desirable features because it is devoid of cavities and is less likely to contain entrapped bubbles of air and/or blood which could affect the mechanical strength of the connection between the implanted portion of the prosthesis and the bone 1.

In a way, the mode of implanting the prosthesis 3 or 3' in the cavity 1a of the bone 1 is reminiscent of the erection of structures by using reinforced concrete. Thus, the framework (including the making of optimal cavity 1a in the bone 1 and introduction and centering of the shank 4 in the cavity 1a) is completed in a first step, and the "pouring" of cement 101 is carried out in the next step with simultaneous evacuation of air from the cavity 1a along the path which is established by the pores or channels of the centering plug 9, lateral port 11, passage 10 and port 12. All this is achieved with the novel expedient of providing the body of the prosthesis 3 with at least one passage 10 which can be located in the central portion or adjacent the external surface 103 of the body of the prosthesis, and of thereupon inserting and centering a selected portion of the body in the cavity 1a so that the pressure upon the marrow 2 does not rise as a result of or during introduction of the shank 4. Furthermore, the pressure upon the marrow 2 does not increase during introduction of flowable cement 101 around the flange 7 and into the cavity 1a because the pressure in the cavity is not above atmospheric pressure.

The shank 4 of the body of the endoprosthesis 3 or 3' can be provided with one or more additional openings or outlets 203, especially in those regions which are close to or immediately adjacent the bone tissue or other tissue surrounding the implanted prosthesis. Such additional outlet or outlets 203 can serve to permit penetration of medicines (such as antibiotics or cytostatics) into contact with the adjacent tissue subsequent to completion of the implanting and setting steps. This reduces the likelihood of or prevents life threatening complications resulting from infections and thus reduces the likelihood of loosening of the implanted prosthesis (such loosening can be a consequence of an infection). Thus, the once established solid and reliable connection between the implanted portion of the body of the prosthesis 3 or 3' and the surrounding portion of the bone 1 remains intact for long periods of time. This holds true for reliability of the connection between the implanted portion of the body of the prosthesis 3 or 3' and the cement 101 as well as for reliability of the connection between the cement 101 and the surrounding bone tissue.

Referring to FIG. 4 there is shown a portion of a spinal column including vertebrae 14 and discs 15 (only one disc is shown). The reference character 16 denotes the spinal cord. A tubular or cylindrical prosthesis 17 is installed in a space (cavity) between two neighboring vertebrae 14, e.g., to replace a damaged vertebra and two damaged discs 15. The prosthesis 17 comprises a centrally located suction passage (not specifically shown) and at least two lateral ports 18 (only one shown) which permit evacuation of air from the passage which is surrounded by the prosthesis and is to be filled with cement.

The prosthesis 17 is fixedly secured to and centered on the adjacent vertebrae 14 by at least two elongated strip-shaped or plate-like connecting or centering members 19 (only one shown in FIG. 4). Screws 19a or analogous fasteners are provided to secure the end portions of the members 19 to the adjacent vertebrae 14. The properly affixed members 19 hold the adjacent vertebrae 14 against angular movement relative to each other. The median portion of each member 19 has an elongated slot 19b for the shanks of screws 19c or other suitable fasteners serving to fix the members 19 to the adjacent portions of the prosthesis 17. Those portions of the prosthesis 17 which are in line with the shanks of the fasteners 19c are preferably provided with predrilled and tapped bores or holes (not shown) to receive the tips of the fasteners 19c.

The connecting and centering members 19 can be provided in addition to or in lieu of additional connecting and centering members 119 in the form of substantially L-shaped brackets each having a first leg affixed to the adjacent vertebra 14 by one or more threaded fasteners 119a and a second leg which extends radially inwardly toward the external surface of the prosthesis 17 to center the latter between the neighboring vertebrae 14. For example, each elongated strip-shaped member 19 can be replaced with two L-shaped members 119 or vice versa.

The temperature of bone cement rises during setting and can be as high as 90° C. Such elevated temperatures could cause injury to the spinal cord 16. Therefore, the structure which is shown in FIG. 4 and includes the prosthesis 17 and the connecting and centering members 19, 119 preferably further comprises means for withdrawing heat from the prosthesis 17 during setting of the introduced cement so as to prevent injury to the spinal cord 16. The illustrated cooling means comprises two portions, sections or shells 20, 21 of a jacket which is placed around the external surface of the prosthesis 17, at least during and for a period after introduction of bone cement. The two sections 20, 21 of the jacket prevent radiation of heat from the prosthesis 17 toward the spinal cord 16 during setting of bone cement.

The shells 20, 21 of the illustrated jacket are provided with openings 22 (only one shown) which register with the lateral ports 18 of the prosthesis 17 when the latter is properly secured between the neighboring vertebrae 14 and the jacket 20, 21 is assembled to surround the properly inserted prosthesis 17. The jacket can be made, at least in part, of a suitable thermally insulating material. Alternatively, the jacket can be provided with cooling means so as to withdraw heat which develops during setting of cement which fills the cavity defined by the properly inserted prosthesis 17. FIG. 4 shows, by broken lines a meandering channel 120 which is provided in the shell 20 of the two-piece jacket and has two open ends 121 (one shown) one of which admits a coolant from a suitable source, not shown, and the other of which discharges spent coolant for disposal or for reuse (e.g., by conveying spent coolant through a suitable heat exchanger, not shown). It is equally possible to employ a jacket whose shells 20, 21 constitute thermal insulators and, in addition, are provided with cooling means 120–121 or analogous cooling means to prevent overheating of the spinal cord 16 during setting of cement which is admitted into the cavity defined by the inserted prosthesis 17.

The shells 20, 21 of the illustrated jacket can be removed when the setting of introduced cement is completed. The closed external surface of the prosthesis 17 and the removability of the jacket including the shells 20, 21 ensure that the dimensions of the hardened cement match the desired optimum values not later than when the jacket is removed from the area around the implanted prosthesis 17. Thus, neither the hardened cement nor the jacket 20, 21 (which is preferably removable) can harm the spinal cord 16 once the setting of bone cement is completed. If the jacket (including the shells 20, 21 or an analogous jacket) is relatively soft, it can remain in the operative position, in which it surrounds the implanted prosthesis 17, without injuring the surrounding tissue including that of the vertebrae 14 or other parts of the body of a patient around the prosthesis 17.

The bone cement filling the cavity which is defined by the prosthesis 17 (with or without the jacket 20, 21) can contain antibiotics and/or cytostatics and/or other medications. To this end, the prosthesis 17 can be provided with one or more outlets 117 (one indicated by broken lines) which permit penetration of such medications from the hardened cement into the adjacent (surrounding) tissue. The outlet or outlets 117 can constitute the interstices of a grid-shaped or lattice-like prosthesis which replaces the illustrated prosthesis 17. If the prosthesis 17 is replaced with a grid-shaped, lattice-like or analogous multiapertured prosthesis, the numerous interstices of such prosthesis are sealed or closed by the jacket 20, 21 or an analogous jacket during admission of bone cement and during subsequent setting of introduced cement, and the jacket is thereupon removed in order to ensure that the medication or medications which are confined in the hardened cement can come in contact with the adjacent tissue. In other words, the properly applied jacket 20, 21 permits evacuation of air only through one or more lateral ports corresponding to the illustrated port 18, but the interstices of the lattice-like or analogous implanted prosthesis permit a large-area contact between the medication-containing hardened bone cement and the adjacent tissue when the jacket is removed subsequent to adequate setting of the cement.

The jacket including the sections 20, 21 or an otherwise configured jacket can serve the additional purpose of overlying or surrounding all sharp edges or protuberances of the prosthesis 17 prior to and during introduction of cement so that the jacket constitutes a protective shroud which eliminates the likelihood of damage to adjacent tissue as a result of contact with sharp portions of the inserted prosthesis. Such function can be performed in addition to the aforediscussed function or functions of the jacket, particularly that of preventing overheating of the spinal cord 16, either by constituting a thermal insulator or by forming part of means for actually cooling the adjacent areas, particularly the introduced cement whose polymerization can result in a pronounced rise of temperature, even all the way to 90° C. which could result in damage to the spinal cord 16.

The connecting and centering members 19 and/or 119 can be omitted, or the number of such members can be reduced if the prosthesis 17 is provided with suitable sockets 217, taped bores or like means for receiving fasteners which are driven into the adjacent bones, such as the vertebrae 14 shown above and below the prosthesis 17 in FIG. 4. The fasteners can constitute screws, bolts, pins or any other suitable parts which can ensure adequate centering of the prosthesis 17 preparatory to and during admission of a requisite quantity of flowable cement into the cavity or cavities defined by the prosthesis between the adjacent bones 14.

A lattice-like or a similar prosthesis renders it possible to even more reliably implant the prosthesis in the cavity of a bone or between the bones of a spinal column. Thus, such a prosthesis can exhibit a stiffness which reduces the likelihood of damage to the connection between the implanted prosthesis and the bone or bones because the thermal expansion coefficient of the implanted prosthesis can be selected to match or to closely approximate that of the adjacent bone or bones and/or that of the cement.

The interior of a hollow prosthesis can be filled with a lattice-like, grid-like or other suitable skeleton frame and the remainder of such interior can be filled with one or more substances which impart to the prosthesis desirable mechanical and other characteristics in order to enhance the strength of the prosthesis and/or of the connection between the prosthesis and the adjacent bone or bones.

The legend "FILLER" is intended to denote in FIG. 1 that the passage 10 can contain a material having the consistency of frit and permitting the flow of viscous cement and/or air. Such filler can reinforce the prosthesis and can also serve to store a supply of medication which is gradually diffused into the bone 1. The filler can be said to constitute a stabilizing core.

FIG. 5 illustrates an implement 30 which can be used to indicate the locus of the tip of the shank 4 and of the plug 9 in the cavity 1a of a bone 1 (e.g., a femur). Such implement can be utilized to facilitate the drilling of one or more bores or holes 1A into the bone 1 at an optimum location with reference to the tip of the properly inserted shank 4 and the centering plug 9. The indicating implement 30 is a substantially U-shaped tool having a first leg 31 extending into the cavity 1a and having a free end at the plug 9. The second leg 32 of the implement 30 is adjacent the outer side 1d of the bone 1 and its free end assumes a predetermined (known) position relative to the free end of the leg 31. The web 33 of the implement 30 can be temporarily affixed to the flange 7 and/or head 6 of the prosthesis 3". When the shank 4 and the centering plug 9 are properly installed in the cavity 1a, the position of the free end of the leg 32 is indicative of the position of the free end of the concealed leg 31. This enables the surgeon in charge to drill one or more bores or holes 1A into the bone 1 at an optimum location for evacuation of air from the cavity 1a so that flowable cement 101 can be admitted at the open end 1b of the cavity 1a. An advantage of the structure which is shown in FIG. 5 is that the shank 4 and other parts of the body of the prosthesis 3" need not be weakened by the provision of one or more passages and/or one or more ports. The free end of the leg 31 of the indicating implement 30 can be temporarily anchored in the centering plug 9 during introduction of the plug 9 into the cavity 1a through the open end 1b. Each of the legs 31, 32 can constitute or resemble an elongated rod. The bore(s) or hole(s) 1A can be provided in the bone 1 in such position or positions that air which fills the cavity 1a between the plug 9 and the open end 1b can be evacuated through the pores of the plug 9. The hole or holes 1A can be provided in addition to the passage 10 and ports 11, 12 to permit simultaneous evacuation of air through the passage 10 and hole or holes 1A.

It is further within the purview of the invention to assemble the improved prosthesis of two or more parts which are articulately connected to each other. This renders it possible to avoid the development of peak stresses in regions where the surrounding tissue is supposed or compelled to yield but a one-piece prosthesis would fail to yield. In such instances, the separately produced and articulately connected parts of the composite prosthesis are required to take up less pronounced stresses because the articulate connection or connections can yield, when necessary, in order to conform the shape of the implanted composite prosthesis to the shape of the adjacent bone or bones. The arrangement may be such that the separately produced parts of the composite prosthesis take up stresses or forces acting in certain first directions whereas the joint or joints (e.g., hinges, spherical joints or the like) take up forces acting in certain second directions. Each part of a composite prosthesis can be provided with one or more suction passages corresponding to the passage 10.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A prosthesis for implantation into at least one bone, comprising an elongated implant body having an external surface, a proximal end and a distal end and being provided with at least one elongated at least substantially sealed suction passage extending between said proximal end and said distal end, said implant body further having at least one first port for admission of a flowable substance into said suction passage at said distal end and said at least one first port communicating with a space at least partially surrounding said external surface and being surrounded by the at least one bone upon introduction of said distal end and of said external surface into the at least one bone, said implant body further having at least one second port for evacuation of a flowable substance from said at least one suction passage and said at least one second port being disposed at said proximal end and being connectable with a suction generating device to draw flowable substance into said at least one suction passage by way of said at least one first port and to thus draw a flowable bone cement into said space as a result of the establishment of a negative pressure in said space.

2. The prosthesis of claim 1, wherein said implant body is of one piece between said first and second ports.

3. The prosthesis of claim 1, wherein said implant body has a plurality of elongated sections and said at least one suction passage is provided in one of said sections.

4. The prosthesis of claim 1, wherein said at least one, suction passage is disposed at least substantially centrally of said implant body.

5. The prosthesis of claim 1, wherein said at least one suction passage is located nearer to a first portion than to a second portion of said external surface.

6. The prosthesis of claim 1, wherein said implant body comprises separable first and second elongated sections and said at least one suction passage is provided in one of said sections.

7. A prosthesis for implantation into a bone, comprising an implant body having an external surface, a proximal end, a distal end, at least one suction passage cooperating with said implant body, and suction ports disposed in said external surface, said suction ports communicating with said at least one suction passage of said implant body; and at least one centering element for centering said implant body in the bone, said centering element being positioned at said distal end of said implant body and comprising a substantially impermeable first portion disposed at a first distance from said proximal end and a permeable second portion disposed at a second distance from said proximal end, said second distance being smaller than said first distance and at least said second permeable portion of said centering element having a microporous structure.

8. A method of introducing an initially flowable and subsequently hardenable bone cement into a space at least partially surrounding an external surface of an elongated implant body which is located in at least one bone, which has at least one elongated at least substantially sealed suction passage, at least one first port establishing a first path for the flow of a flowable substance from said space into said at least one suction passage at a distal end of said implant body, and at least one second port for evacuation of said flowable substance from said suction passage at a proximal end of said implant body, comprising the steps of pneumatically evacuating said flowable substance from said space by way of said at least one first port, said at least one suction passage and said at least one second port; and establishing a second path for automatic admission of flowable bone cement into said space as a result of pneumatic evacuation of said flowable substance from said space by way of said at least one first port, said suction passage and said at least one second port and the ensuing establishment of a negative pressure in said space.

* * * * *